US 11,759,538 B2

(12) United States Patent
Gal et al.

(10) Patent No.: US 11,759,538 B2
(45) Date of Patent: Sep. 19, 2023

(54) DOOR LOCKING MECHANISM FOR A STERILIZER

(71) Applicant: SciCan Ltd., Toronto (CA)

(72) Inventors: Stelian Gabriel Gal, Scarborough (CA); Gabriel Neagoe, Richmond Hill (CA)

(73) Assignee: SciCan Ltd., Toronto (CA)

( * ) Notice: Subject to any disclaimer, the term of this patent is extended or adjusted under 35 U.S.C. 154(b) by 212 days.

(21) Appl. No.: 17/241,713

(22) Filed: Apr. 27, 2021

(65) Prior Publication Data

US 2022/0339311 A1 Oct. 27, 2022

(51) Int. Cl.
*A61L 2/26* (2006.01)
*E05B 65/46* (2017.01)
*E05B 47/00* (2006.01)

(52) U.S. Cl.
CPC .......... *A61L 2/26* (2013.01); *E05B 65/46* (2013.01); *A61L 2202/121* (2013.01); *E05B 2047/005* (2013.01); *E05B 2047/0067* (2013.01)

(58) Field of Classification Search
CPC ............ E05B 65/00; E05B 65/46; E05B 65/461–463; E05B 65/465–466; E05B 2047/0048; E05B 2047/005; E05B 2047/0051–0056; E05B 2047/0067–0069; E05B 17/047; E05B 17/048; E05B 81/64; E05B 81/66; E05B 81/68; A61L 2/26; A61L 2202/121
USPC .......................................................... 70/263
See application file for complete search history.

(56) References Cited

U.S. PATENT DOCUMENTS

| | | | |
|---|---|---|---|
| 2,898,138 A * | 8/1959 | Van ................. | E05B 47/0012 |
| | | | 292/201 |
| 2,898,139 A | 8/1959 | Van Noord | |
| 4,543,748 A | 10/1985 | North, Jr. | |
| 4,915,913 A * | 4/1990 | Williams ............. | B65D 45/24 |
| | | | 436/1 |
| 4,932,160 A | 6/1990 | Sperko | |
| 5,517,006 A | 5/1996 | Fredriksson | |

(Continued)

FOREIGN PATENT DOCUMENTS

| CN | 210145148 U | 3/2020 |
|---|---|---|
| GB | 1217989 A | 7/1971 |

(Continued)

OTHER PUBLICATIONS

International Search Report(ISR) and Written Opinion (WO) for PCT/CA2022/050639 dated Jul. 29, 2022.

*Primary Examiner* — Nathan Cumar

(57) ABSTRACT

A door locking mechanism for a sterilizer that minimizes the occurrence of jamming during operation, and that can be manually actuated if necessary. The door locking mechanism abuts the door of the sterilizer, and comprises a hingedly connected locking arm to permit the locking arm to move between a locked position and an unlocked position. A sensor arm arranged adjacent to the locking arm detects pressure from from an extendible portion of the door as it engages the locking mechanism. The sensor arm causes the actuation of a motor that permits the locking arm to move from the unlocked position to the locked position, in which the locking arm engages and retains the extendible portion to secure the closure of the door.

15 Claims, 12 Drawing Sheets

(56) References Cited

U.S. PATENT DOCUMENTS

| | | | | |
|---|---|---|---|---|
| 6,391,258 B1* | 5/2002 | Peake | ............ | B01J 3/03 |
| | | | | 292/201 |
| 7,951,342 B2* | 5/2011 | Benning | ............ | A61L 2/24 |
| | | | | 422/26 |
| 2016/0130840 A1* | 5/2016 | Garneau | ............ | E05B 47/0012 |
| | | | | 292/201 |

FOREIGN PATENT DOCUMENTS

| | | | |
|---|---|---|---|
| JP | 11192289 A | | 7/1999 |
| JP | 11264469 A | | 9/1999 |
| JP | 2006149789 A | * | 6/2006 |
| JP | 2006149789 A | | 6/2006 |
| JP | 2012090706 A | | 5/2012 |
| JP | 2013102816 A | | 5/2013 |
| JP | 5723748 B2 | | 5/2015 |

* cited by examiner

DOOR LOCKING MECHANISM FOR A STERILIZER

FIELD OF THE INVENTION

The present invention relates to sterilizers, such as for medical and dental articles, and more particularly, for a door locking mechanism for the sterilizer.

BACKGROUND OF THE INVENTION

Sterilizers are widely used in places such as medical and dental offices, and research laboratories, to sterilize reusable articles. Based on space and cost constraints, sterilizers come in many sizes, including smaller benchtop sterilizers. Regardless, of size, sterilizers typically have a door that provides access to the interior sterilizer chamber to allow for placing and removing articles. The interior chamber becomes steam filled during operation, and a heater is typically located within the chamber for increasing the temperature and pressure to sterilize the articles. Some sterilizers include features that can perform a drying cycle prior to removal of the articles.

During the sterilization cycle, temperature and pressure inside the chamber will reach high levels (e.g. 135° C. and 300 kPa) sufficient to ensure that the deactivation and/or killing of pathogenic microorganisms is fully accomplished. However, due to the high temperature and pressure, it is paramount for safety reasons that the door of sterilizer be secured in the closed position, ideally until the interior pressure is 5 kPa or less above atmospheric pressure.

Sterilizer door locking mechanisms can face multiple issues during operation, such as jamming while in the closed and locked position. This often occurs due to the high forces the pressure and temperature places on the locking mechanism, which increases friction forces that exceed what the door-actuating device can handle. This makes it desirable for the user to be able to manually actuate the locking mechanism to open the door.

A number of sterilizer locking mechanisms have been described in the art, for example, U.S. Pat. Nos. 7,951,342, 5,517,006, 4,932,160, 2,898,138, 4,543,748, 6,391,258, JP 5,723,748, JP 11264469, JP 11192289, JP 2006149789, and GB 1,217,989.

There is a need in the industry to have a secure sterilizer door locking mechanism that reduces the occurrence of jamming during operation, and that can be manually actuated if necessary.

SUMMARY OF THE INVENTION

According to an aspect of the present invention, there is provided a door locking mechanism for a sterilizer, the door locking mechanism abutting the door of the sterilizer, and comprising: a locking arm hingedly connected to a frame to permit the locking arm to move between a locked position and an unlocked position, the locking arm having a cutaway portion, the cutaway portion permitting an extendible portion of the door to extend therethrough; a sensor arm arranged adjacent to the locking arm, the sensor arm being flexible to permit the sensor arm to be at least partially displaced away from the locking arm in response to applied pressure to the sensor arm from the extendible portion of the door as it passes through the cutaway portion; a motor in communication with the operating system; a camshaft actuated by the motor; a cam attached to the camshaft, the cam being in contact with the locking arm to move the locking arm between the locked position and the unlocked position; a closing switch positioned within the locking mechanism to detect displacement of the sensor arm, the closing switch being in communication with an operating system of the sterilizer such that when the closing switch detects displacement of the sensor arm it signals to the operating system that the door is in a latched position; and a locking switch positioned within the locking mechanism to detect movement of the locking arm into the locked position, the locking switch being in communication with the operating system such that when the locking switch detects the movement of the locking arm into the locked position it signals to the operating system that the door is in the locked position.

In an embodiment, the locking arm has a first end, a second end, and a middle portion, the first end hingedly connected to the frame, the second end having the cutaway portion and being shaped and dimensioned to engage with and retain the extendible portion in an extended position, and the middle portion having an upper member and a lower member, each protruding outward from the locking arm.

In an embodiment, the sensor arm has a first end and a second end, the second end configured to be at least partially displaced away from the second end of the locking arm in response to applied pressure to the second end of the sensor arm from the extendible portion of the door as it passes through the cutaway portion.

In an embodiment, the cam is in contact with the upper member to move the locking arm.

In an embodiment, the locking switch detects the lower member moving into the locked position.

In an embodiment, the door locking mechanism further comprises a resilient member connected at a first end to the locking arm, and at the second end to the frame, the resilient member biasing the locking arm downward into a locked position.

In an embodiment, the door locking mechanism further comprises a manual release lever extending downward from the locking arm, whereby movement of the manual release lever rotates the locking arm between the locked position and the unlocked position. The manual release lever preferably extends downward from a first end or a second end of the locking arm.

In an embodiment, the closing switch comprises a sensing lever, one end of the sensing lever being biased away from the closing switch, and wherein depression of the sensing lever by the sensor actuates the closing switch.

In an embodiment, the locking switch comprises a locking switch sensing lever, one end of the locking switch sensing lever being biased away from the locking switch, and wherein depression of the locking switch sensing lever by the lower member actuates the locking switch.

In an embodiment, the door locking mechanism comprises more than one of the closing switches and/or the locking switches.

In an embodiment, at least the second end of the sensor arm substantially mirrors the shape of the second end of the locking arm except for the cutaway portion.

In an embodiment, the first end of the sensor arm is fastened to the locking arm, or the first end of the sensor arm is hingedly attached to the same point of the frame as the locking arm.

In an embodiment, the cam is an eccentric cam, a pear shaped cam, a snail shaped cam, or an elliptical shaped cam.

According to another aspect of the present invention, there is provided a door locking mechanism for a sterilizer, the door locking mechanism abutting the door of the sterilizer, and comprising: a locking arm having a first end, a second end, and a middle portion, the first end hingedly connected to a frame to permit the locking arm to move between a locked position and an unlocked position, the second end having a cutaway portion, the cutaway portion permitting an extendible portion of the door to extend therethrough, the second end being shaped and dimensioned to engage with and retain the extendible portion in an extended position, and the middle portion having an upper member and a lower member, each protruding outward from the locking arm; a resilient member connected at a first end to the locking arm, and at the second end to the frame, the resilient member biasing the locking arm downward into a locked position; a manual release lever extending downward from the locking arm, whereby movement of the manual release lever rotates the locking arm between the locked position and the unlocked position; a sensor arm having a first end and a second end and arranged adjacent to the locking arm, the sensor arm being flexible to permit the second end of the sensor arm to be at least partially displaced away from the second end of the locking arm in response to applied pressure to the second end of the sensor arm from the extendible portion of the door as it passes through the cutaway portion; a motor in communication with the operating system; a camshaft actuated by the motor; a cam attached to the camshaft, the cam being in contact with the upper member to move the locking arm between the locked position and the unlocked position; at least one closing switch positioned within the locking mechanism to detect displacement of the sensor arm, the closing switch being in communication with an operating system of the sterilizer such that when the closing switch detects displacement of the sensor arm it signals to the operating system that the door is in a latched position; and at least one locking switch positioned within the locking mechanism to detect movement of the lower member into the locked position, the locking switch being in communication with the operating system such that when the locking switch detects the movement of the lower member into the locked position it signals to the operating system that the door is in the locked position.

BRIEF DESCRIPTION OF THE DRAWINGS

Reference will now be made, by way of example, to the accompanying drawings which show example embodiments of the present application, and in which.

DETAILED DESCRIPTION OF THE PREFERRED EMBODIMENTS

The following detailed description of the preferred embodiment(s) is merely exemplary in nature and is in no way intended to limit the invention, its application, or uses. While but a single embodiment of the present invention has generally been herein shown and described, it will be understood that various changes may be made without departing from the scope of the invention.

Figure 1:
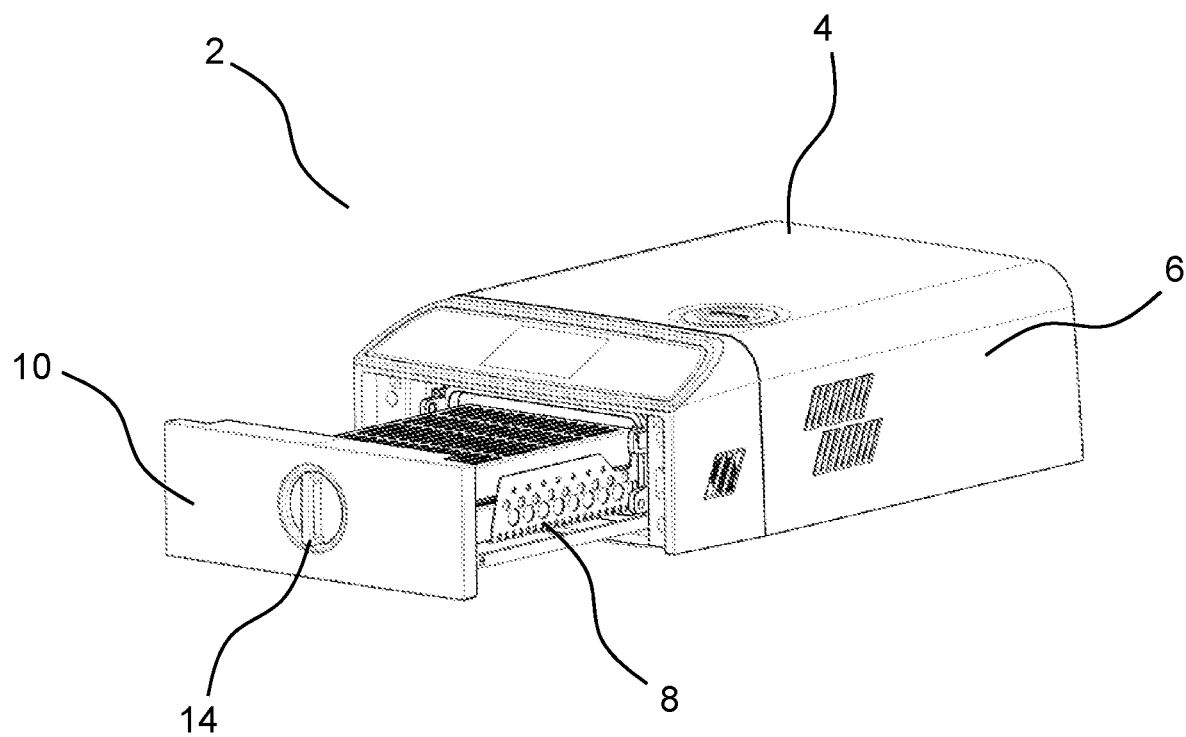
FIG. 1 is a front perspective view of an exemplary sterilizer.

FIG. 1 illustrates a known benchtop sterilizer 2, having a main body 4 that includes the interior sterilizing chamber and the necessary components to operate the sterilizer 2, and an outer casing 6. A drawer 8 can be used for inserting articles into the interior sterilizing chamber. In this version of the sterilizer 2, a door 10 is attached to the front of the drawer 8 and closes when the drawer 8 is fully entered into the chamber. Alternative versions of sterilizers 2 may have a door hingedly attached that swings between open and closed positions.

Figure 2:
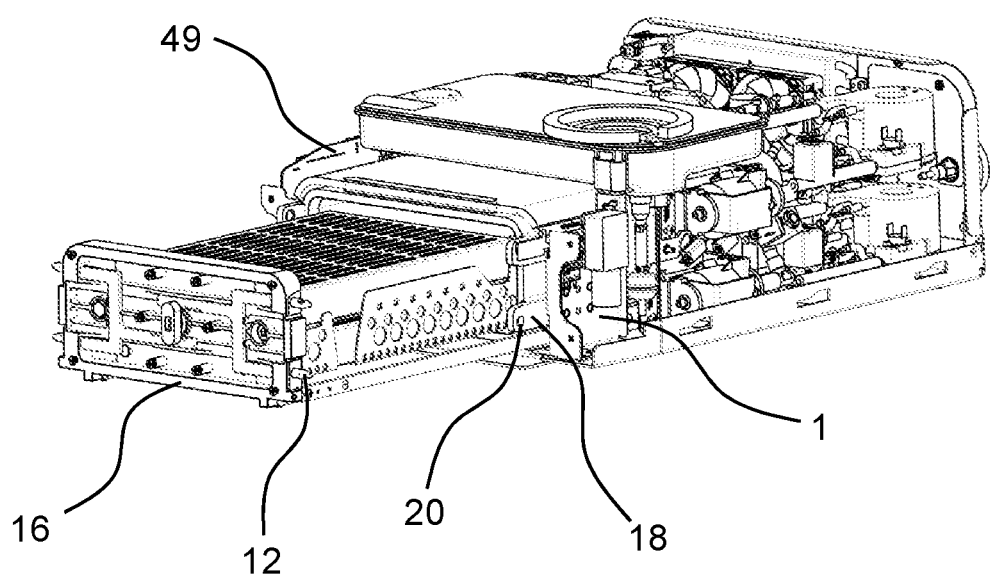
FIG. 2 is a front perspective view of the sterilizer shown in FIG. 1, in which the outer casing has been removed to illustrate an embodiment of the locking mechanism.
Figure 3:
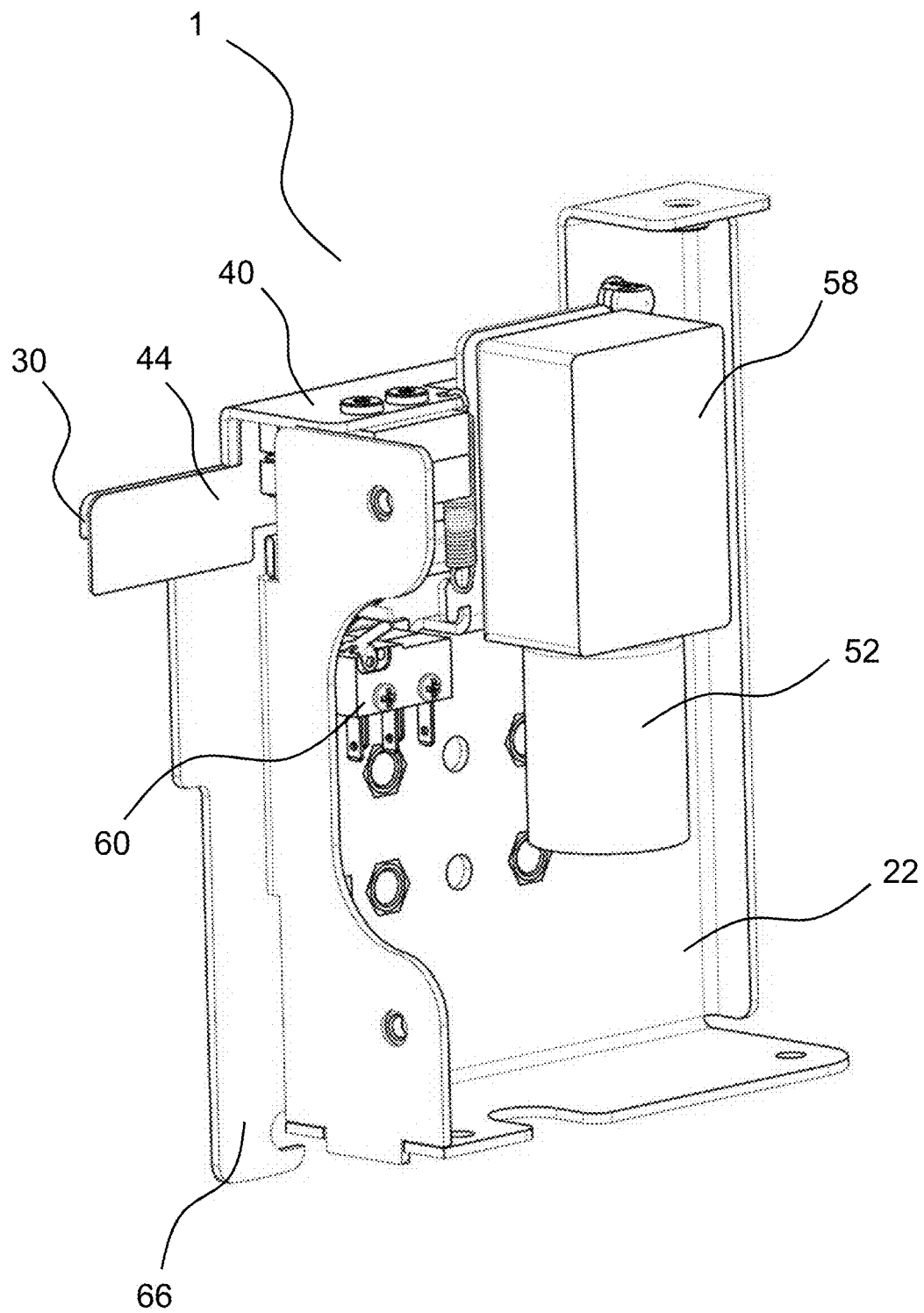
FIG. 3 is a front perspective view of an embodiment of the locking mechanism.

In FIG. 2, the casing 6 of the entire sterilizer, including the door 10, has been removed, which reveals an extendible portion, such as retractable pins 12 located at the side face of the door 10. The pins 12 can be found on one or both sides of the door 10, and the number of pins 12 on each side of the door 10 may vary. For example, a taller door 10 would employ more pins 12 than the relatively shorter door 12 shown in FIGS. 1 and 2.

As can be seen in FIGS. 1 and 2, there is a knob 14 on the front face of the drawer 8 that in this embodiment controls the deployment and retraction of the pins 12. A rotating movement of the knob 14 in the clockwise direction deploys the pins 12 out of the door 10, while a rotating movement of the knob 14 in the counter clockwise direction retracts the pins 12 back into the door 10. Other mechanisms known in the art that can retract and deploy the pins 12 in a similar manner may also be employed.

Figure 8A:
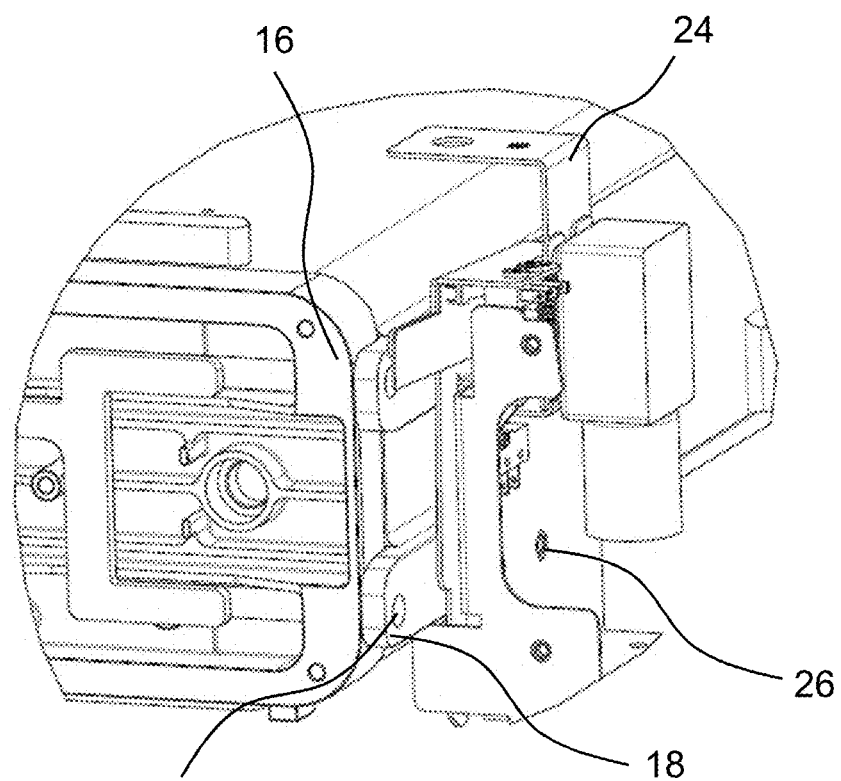
FIG. 8A is a partial view of a sterilizer illustrating an embodiment of the locking mechanism, in which the door is in the unlatched and unlocked position.

In FIG. 8A, the drawer 8 is shown in the closed position. In this position, the frame 16 of the door 10 abuts guides 18 that extend from the main body 4 of the sterilizer 2. The frame 16 of the door 10 contains apertures that allows for the deployment and retraction of the pins 12. Each guide 18 contains a corresponding aperture 20 that is able to receive a pin 12 (see FIG. 9A).

The terminating end of the pins 12 may taper to either a point or a narrower portion, or it may maintain the same cross-sectional area throughout. Furthermore, the pins 12 may have a round cross section as shown in the Figures, or alternatively, the pins may take on other cross-sectional profiles.

Figure 9A:
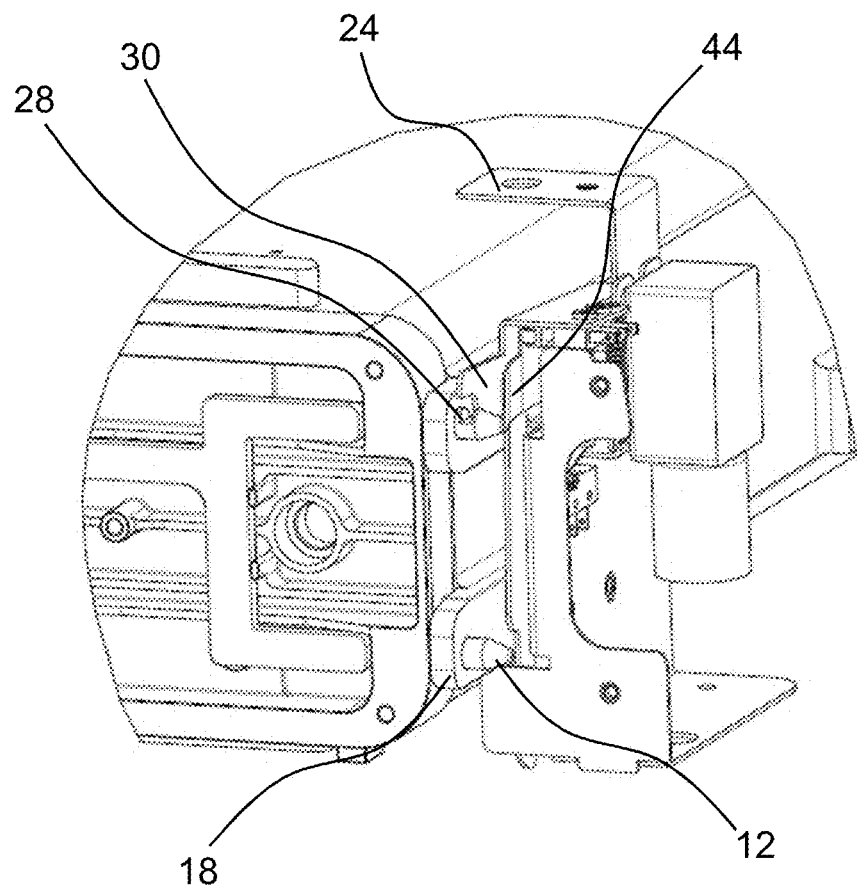
FIG. 9A is a partial view of a sterilizer illustrating an embodiment of the locking mechanism, in which the door is in the latched and unlocked position.

In FIG. 9A, it can be seen that in the terminal portion of the pin 12 that extends through the aperture 20 of the guide 18 is a notch 28, preferably extending through about the upper half of the pin 12. The notch 28 is shaped and dimensioned to receive a locking arm 30 of the locking mechanism. In the embodiments shown in the Figures, only the upper pin 12 is shown as having a notch 28, as this is the only pin 12 that engages with a locking arm 30 of the locking mechanism 1. However, it is contemplated that a sterilizer may incorporate more than one locking mechanism 1, and therefore, each pin 12 that engages with a locking arm 30 from a locking mechanism 1 will include its own notch 28.

Once the pin 12 extends through the guide apertures 20, the locking mechanism 1 is engaged. FIGS. 3 to 6 show the front and rear sides, respectively, of an embodiment of the locking mechanism 1.

Elements of the locking mechanism 1 may be secured directly to a frame 22. The frame 22 may be attached to the main body 4 of the sterilizer 2 via fasteners 26. Alternatively, the elements of the locking mechanism 1 may be secured directly to the outer frame of the sterilizer 2.

The locking mechanism 1 includes the locking arm 30. The embodiment of the locking arm 30 illustrated in FIGS. 3 to 6 is shown in isolation in FIG. 7A. A modified embodiment of the locking arm 30 is shown in isolation in FIG. 7B. As seen in FIG. 5, a first end 32 of the locking arm 30 is hingedly attached to the frame 22 at a hinge point 33. This connection allows the locking arm 30 to rotate about the hinge point 33, thereby allowing the opposing second end 34 of the locking arm 30 to move up and down between an unlocked position and a locked position. The second end 34 of the locking arm 30 ultimately engages with the pin 12, and is shaped and dimensioned to fit within the notch 28 of the pin 12. The second end 34 of the locking arm 30 preferably has a cutaway portion 36, e.g. producing a substantially "L" shaped terminal end. The cutaway portion 36 facilitates nesting of the second end 34 of the locking arm 30 into the notch 28 of the pin 12.

Connecting the first end 32 and the second end 34 of the locking arm is a middle portion 38. Extending inwardly from the middle portion 38 with respect to the locking mechanism 1 is an upper member 40 and a lower member 42. While the upper and lower members 40, 42 are shown as being substantially perpendicular to the middle portion 38 of the locking arm 30, some variation is possible provided the upper and lower members 40, 42 retain their ability to function as discussed below. The middle portion 38 and the upper member 40 may also have connection points for interaction with other components of the locking mechanism 1.

Figure 9B:
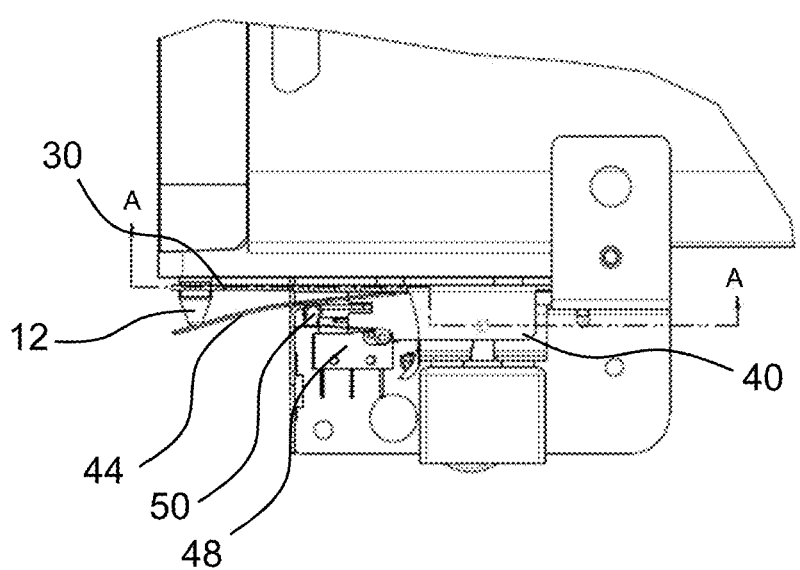
FIG. 9B is a top view of the locking mechanism shown in FIG. 9A, in which the upper member of the locking arm is not shown to improve clarity.

As can be seen in FIGS. 3 to 6, the locking mechanism further comprises a sensor arm 44. A second end of the sensor arm 44 (not shown) is hingedly secured to the frame 22 at the same hinge point 33 as the locking arm 30. Alternatively, the second end of the sensor arm 44 may be secured directly to the first end 32 and/or the middle portion 38 of the locking arm 30, such as with fasteners or rivets. The sensor arm 44 and the locking arm 30 are situation adjacent each other. The opposing first end 46 of the sensor arm 44 is shaped to substantially mirror the shape of at least the second end 34 of the locking arm 30, although the first end 46 of the sensor arm 44 does not include a corresponding cutaway portion 36 as is present in the locking arm 30 (See FIG. 5). In the absence of a corresponding cutaway portion 36 in the sensor arm 44, when the pin 12 extends through the guide apertures 20, it is able to bypass the locking arm 30 and apply pressure to the first end 46 of the sensor arm 44 (See FIGS. 9A and 9B). The sensor arm 44 is preferably flexible, and can be made from a flexible or thin material, such as spring steel. This allows the sensor arm 44 to flex about its second end that is secured to the locking arm 30, such as in response to the pressure applied to the first end 46 of the sensor arm 44 by the pin 12. While the sensor arm 44 is described and shown as substantially mirroring the shape of the locking arm 30, different shapes are possible provided that the pin is able to bypass the locking arm 30, such as through the cutaway portion 36, to engage with the sensor arm 44.

Figure 4:
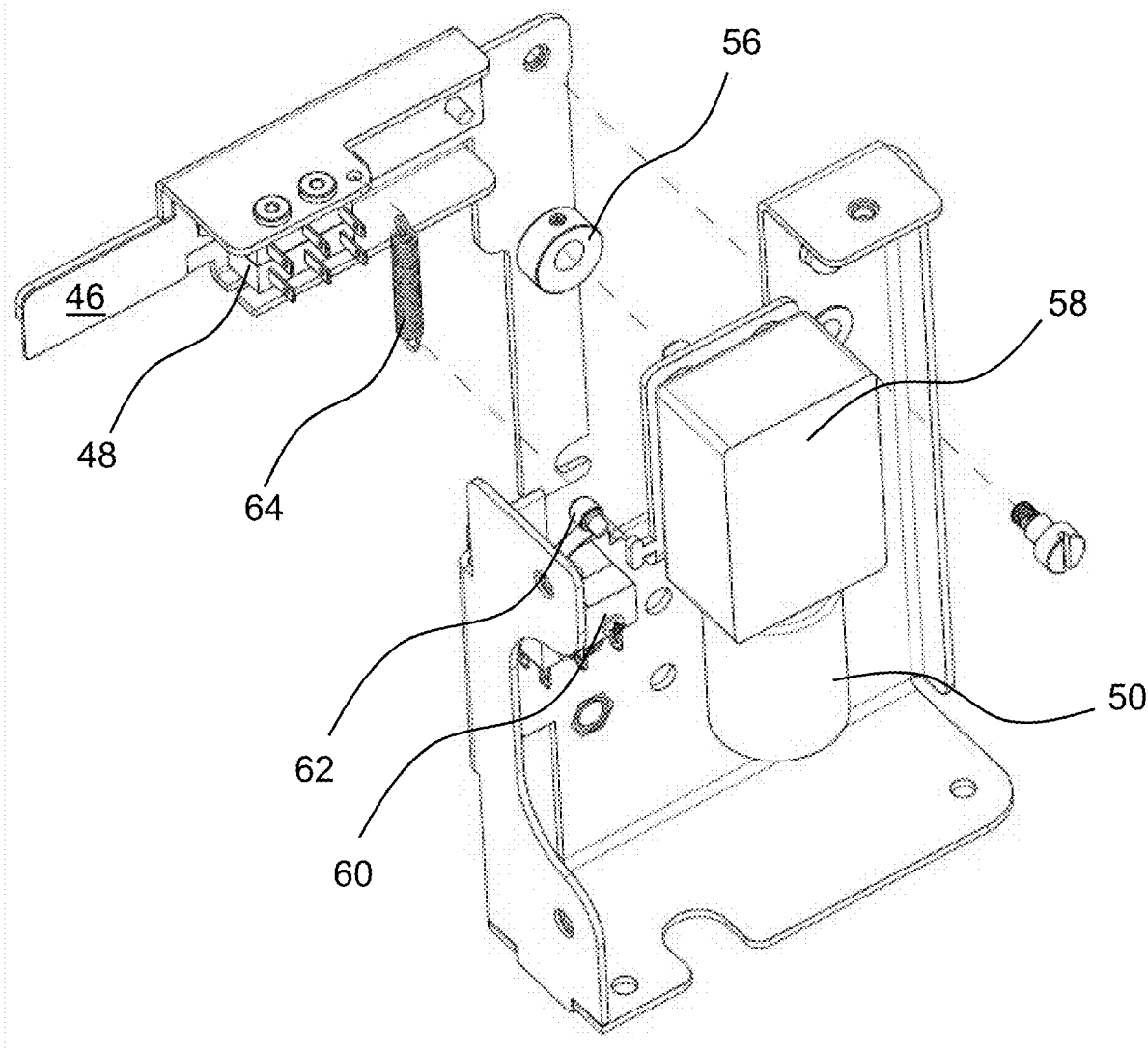
FIG. 4 is an exploded view from the front perspective of an embodiment of the locking mechanism.
Figure 5:
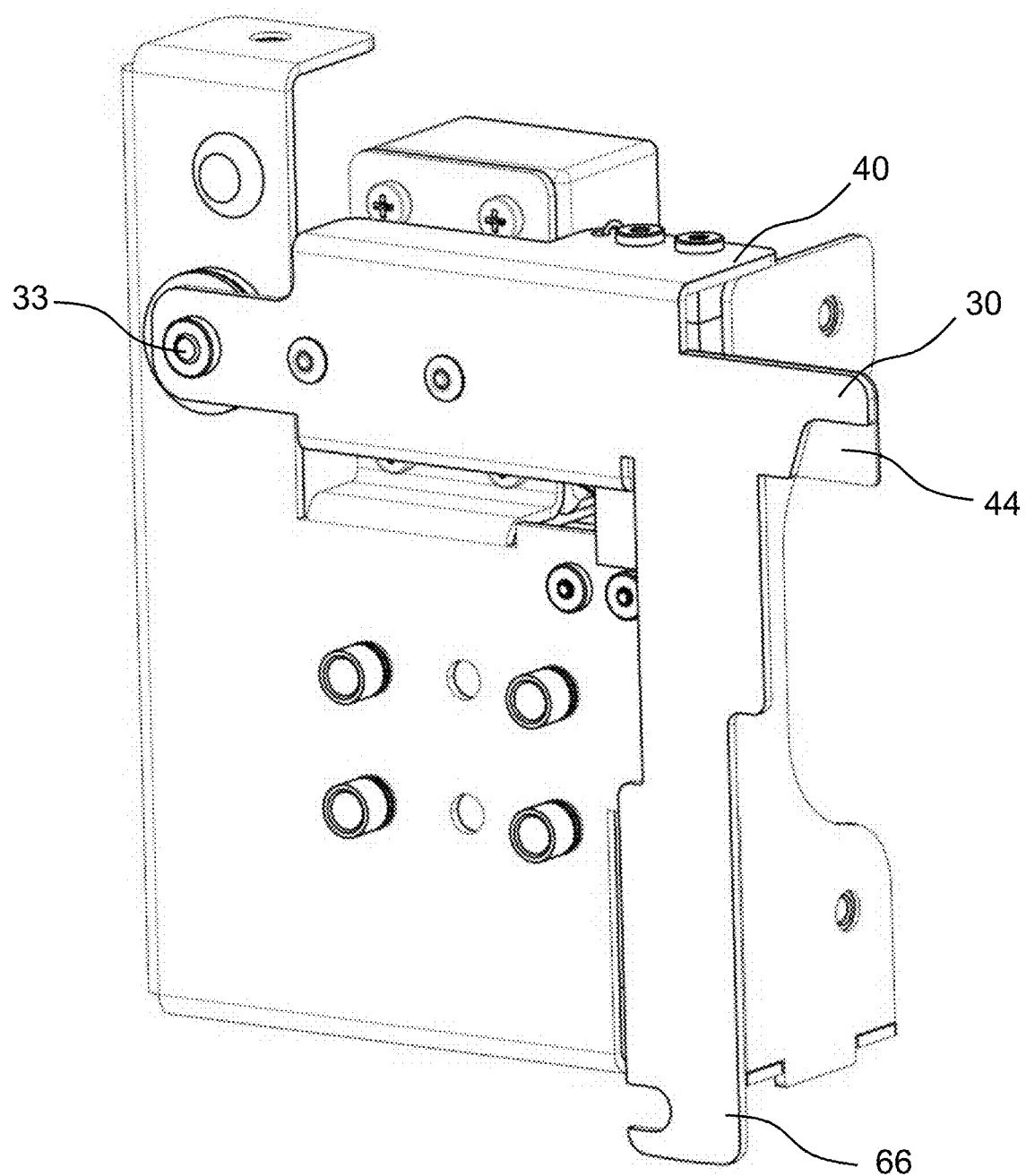
FIG. 5 is a rear perspective view of the locking mechanism shown in FIG. 3.
Figure 6:
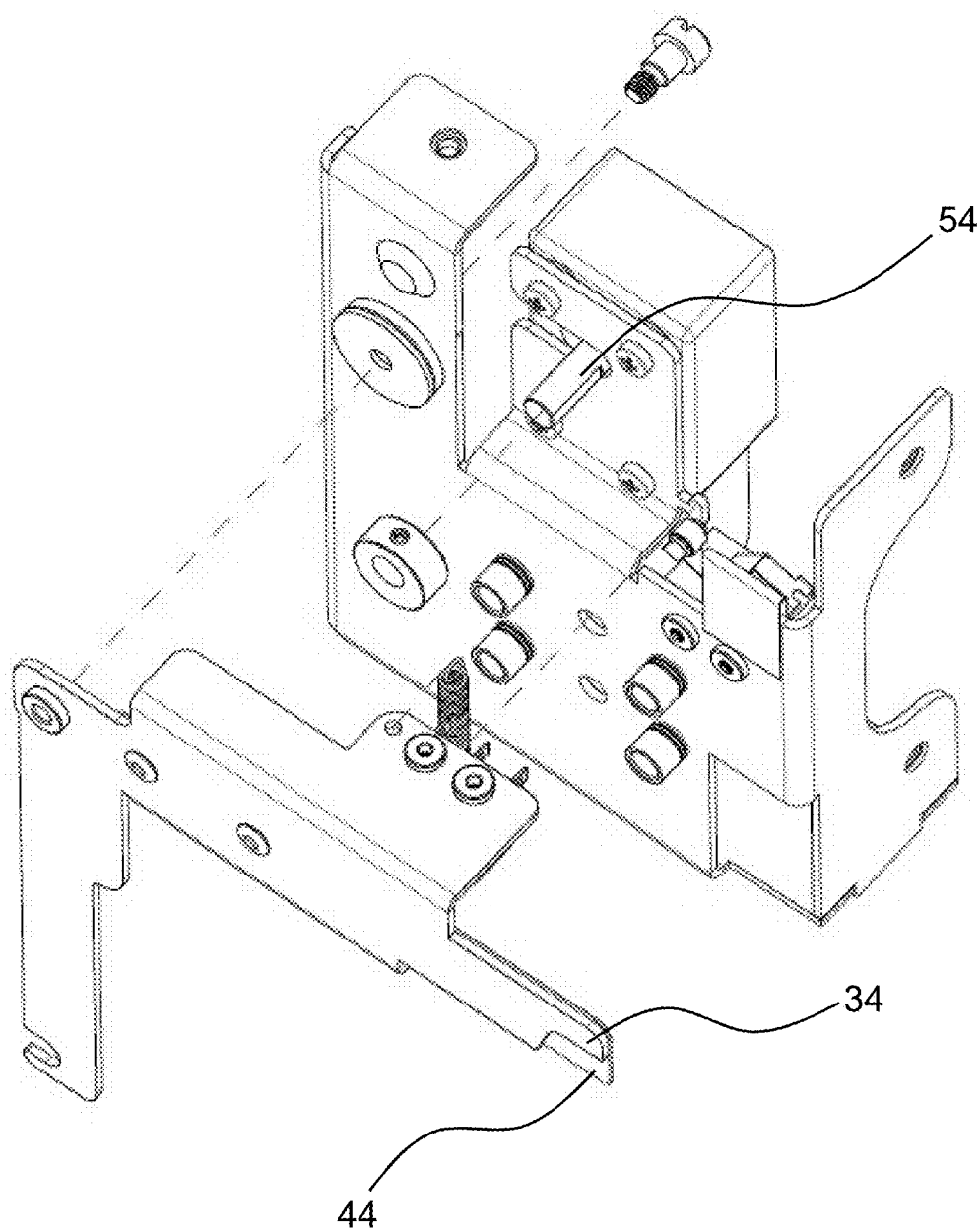
FIG. 6 is an exploded view from the rear perspective of an embodiment of the locking mechanism.

A closing switch 48 forms part of the locking mechanism 1, and can be secured to the upper member 40 of the locking arm 30 as shown in FIG. 4. The closing switch 48 senses a closed state of the door 10 through outward movement of the sensor arm 44. For example, when the door 10 of the sterilizer 2 is closed, the pin 12 extends through the cutaway portion 36 of the locking arm 30 and applies pressure to the first end 46 of the sensor arm 44, causing the sensor arm 44 to flex (See FIGS. 9A and 9B). The flexed sensor arm 44 comes in contact with the closing switch 48, thereby actuating the closing switch 48.

Figure 8B:
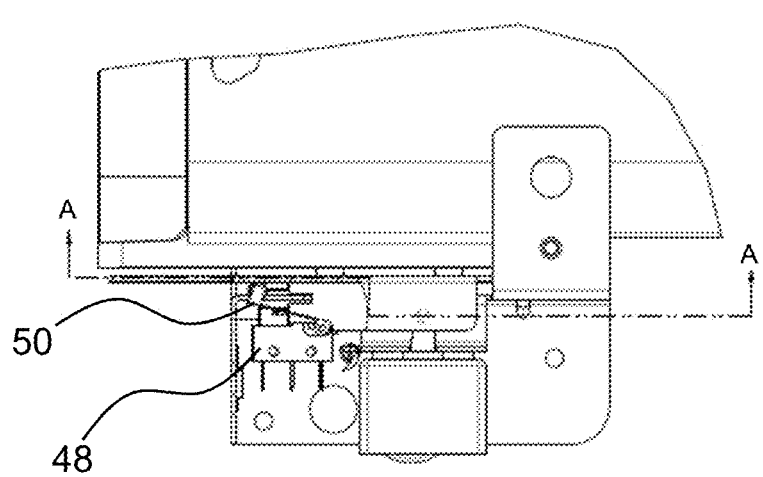
FIG. 8B is a top view of the locking mechanism shown in FIG. 8A, in which the upper member of the locking arm is not shown to improve clarity.

In an alternative embodiment, the closing switch 48 has a lever 50 that is connected at one end to the closing switch 48, while the opposing end is biased away from the closing switch 48 (See FIG. 8B). In this embodiment, the flexed sensor arm 44 comes in contact with the opposing end of the lever 50, which displaces it toward the closing switch 48. Once the lever 50 is moved a predetermined distance toward the closing switch 48, the closing switch 48 is actuated.

Actuation of the closing switch 48 signals an operating system 49 of the sterilizer 2 informing it that the pin 12 is fully deployed and in the latched position. At this point, the operating system communicates with and activates a motor 52 to start the locking sequence. The motor 52 controls the operation of a camshaft 54 and a cam 56 (See FIGS. 4 and 6). The motor is preferably a DC motor that can be equipped with a high ratio gear assembly 58. In the illustrated embodiments, both the motor 52 and the camshaft 54 and cam 56 mechanism are secured to the frame 22, and at least a portion thereof is covered by a housing.

An alternative embodiment employs a two step process. Similar to above, in this embodiment, the knob 14 is turned to deploy the pins 12 and latch the door 10. The pin 12 engages with the sensor arm 44, which ultimately actuates the closing switch 48. Actuation of the closing switch 48 informs the operating system that the pins are fully engaged and the door is latched. However, in this embodiment, the user is required to press a "lock" button on a control panel of the sterilizer 2 to initiate the locking sequence. Once the "lock" button has been pressed, the operating system activates the motor 52 to start the locking system.

Figure 8C:
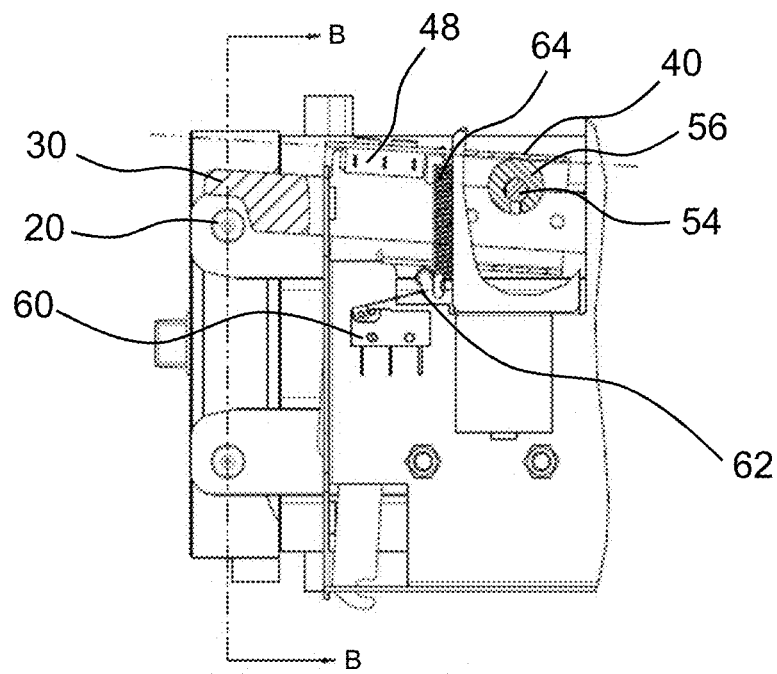
FIG. 8C is a view of the locking mechanism along lines A-A of FIG. 8B, in which an end portion of the sensor arm is not shown to improve clarity.
Figure 8D:
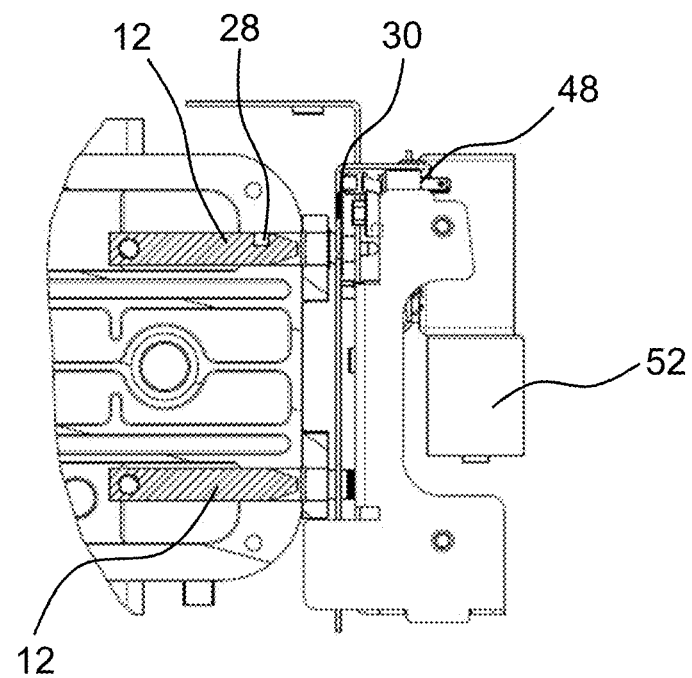
FIG. 8D is a view of the locking mechanism along lines B-B of FIG. 8C.
Figure 9C:
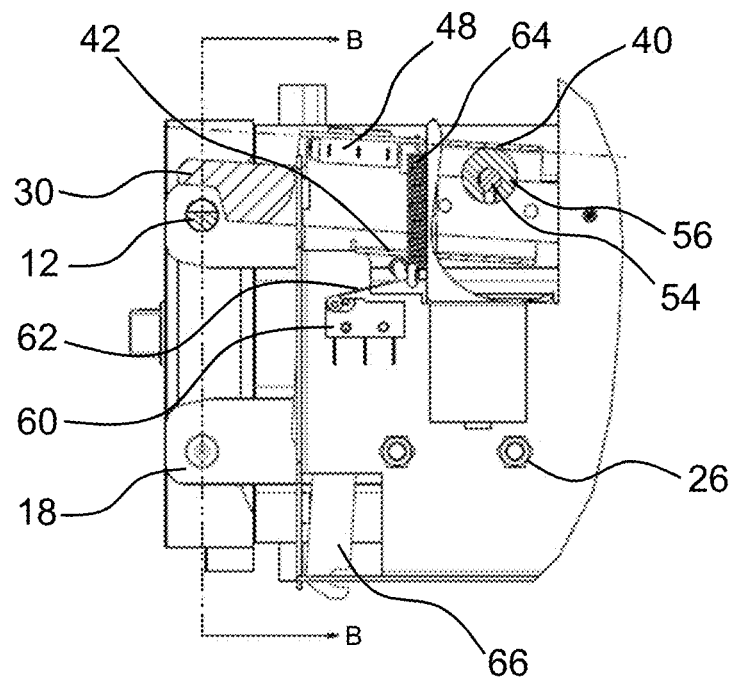
FIG. 9C is a view of the locking mechanism along lines A-A of FIG. 9B, in which a portion of the sensor arm is not shown to improve clarity.
Figure 9D:
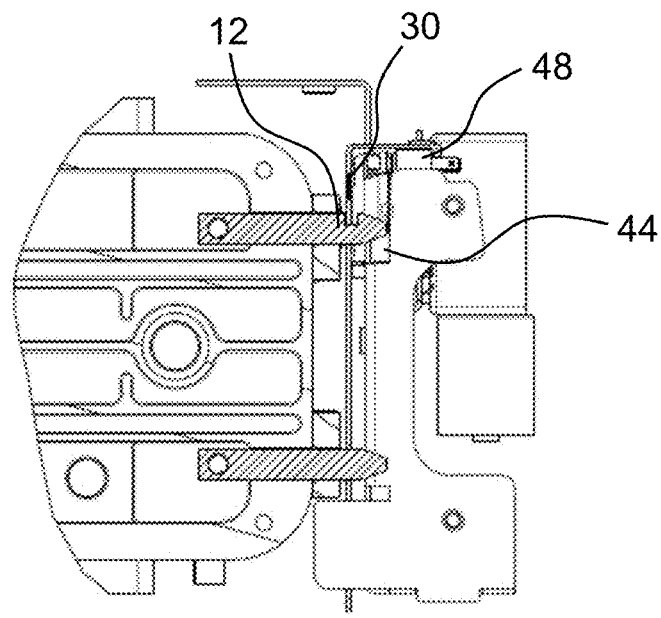
FIG. 9D is a view of the locking mechanism along lines B-B of FIG. 9C.
Figure 10A:
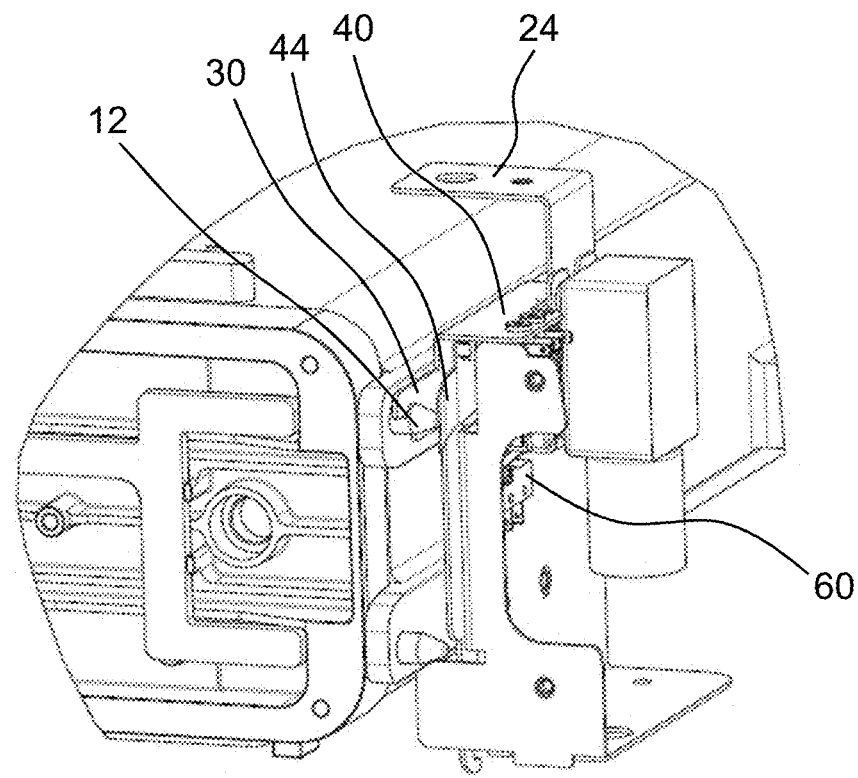
FIG. 10A is a partial view of a sterilizer illustrating an embodiment of the locking mechanism, in which the door is in the fully locked position.
Figure 10B:
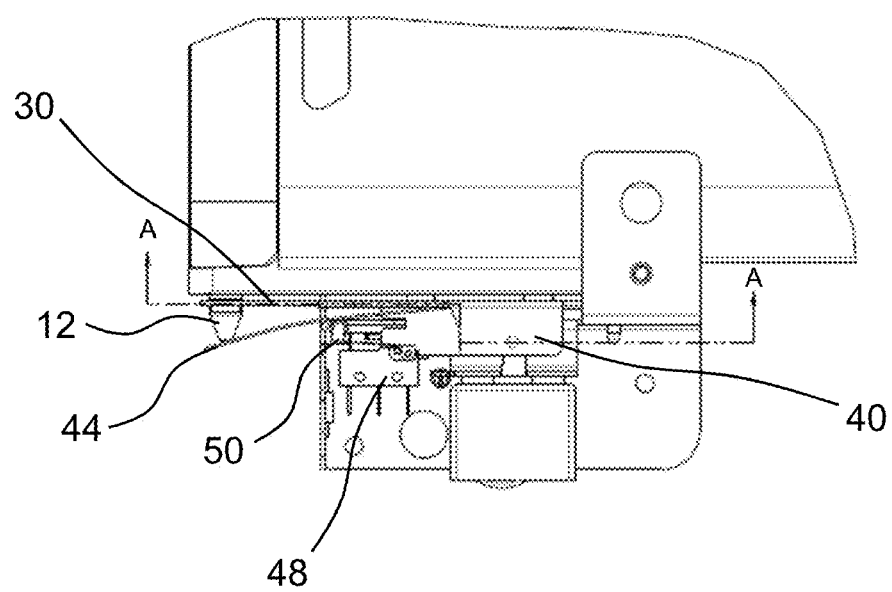
FIG. 10B is a top view of the locking mechanism shown in FIG. 10A, in which the upper member of the locking arm is not shown to improve clarity.
Figure 10C:
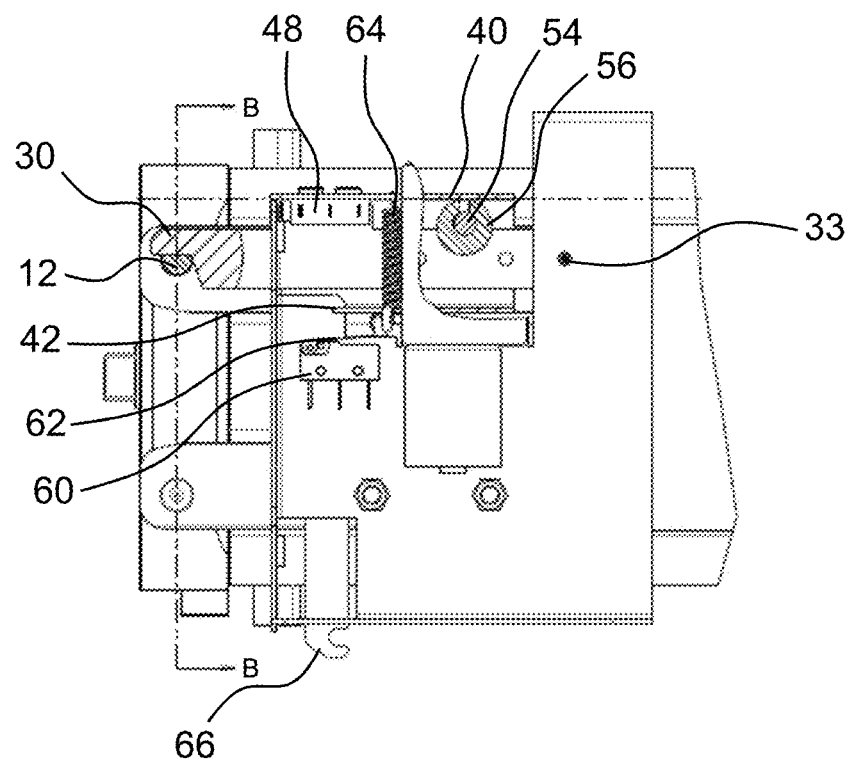
FIG. 10C is a view of the locking mechanism along lines A-A of FIG. 10B, in which a portion of the sensor arm is not shown to improve clarity.

The cam 56 interacts with the upper member 40 of the locking arm 30 (See FIGS. 8C, 9C, and 10C). As the cam 56 rotates via the camshaft 54 and the motor 52, it is able to manipulate the position of the locking arm 30 between an unlocked position (FIGS. 8C and 9C) and a locked position (FIG. 10C).

In the illustrated embodiments, the cam 56 is an eccentric cam in which the cam disc itself is substantially circular, however, the camshaft 54 is attached at a point that is offset from the centre of the cam 56. Such a design allows for rotation of the cam 56 to move the locking arm 30 up and down. The cam 56 may have other designs provided that they translate rotational movement of the cam 56 into up and down movement of the locking arm 30. For example, the cam 56 can have an irregular shape, such as a pear shape, snail shape, elliptical shape, etc. which would accomplish the same function of moving the locking arm 30 up and down in response to rotation of the cam 56.

The locking mechanism 1 also includes a locking switch 60, which as can be seen in FIG. 4, is secured to the frame 22. The locking switch 60 senses when the locking arm 30 is in a locked position. For example, when the locking arm 30 moves downward into a locked position (see FIG. 10*c*), the lower member 42 of the locking arm can come in contact with the locking switch 60, thereby actuating the locking switch 60. Actuation of the locking switch 60 equates with the cam 56 being in substantially the correct position for the locking arm 30 to be in the locked position. The locking switch 60 then communicates with and informs the operating system that the locking arm 30 is in the locked position. The operating system then turns off the motor 52 to cease any further rotation of the camshaft 54.

In an alternative embodiment, the closing switch 60 has a lever 62 that is connected at one end to the locking switch 60, while the opposing end is biased away from the closing switch 60 (see FIGS. 4 and 8C). In this embodiment, when the locking arm 30 is substantially lowered into a locked position, the lower member 42 of the locking arm 30 comes in contact with the opposing end of the lever 62, which displaces it toward the locking switch (See FIG. 10C). Once the lever 62 is moved a predetermined distance toward the locking switch 60, the locking switch 60 is actuated.

The locking mechanism 1 may operate with a single closing switch 48 and locking switch 60. However, it is contemplated that the locking mechanism 1 may have more than one closing switch 48 and/or locking switch 60. See for example FIG. 4, which illustrates a locking mechanism 1 having two closing switches 48 and two locking switches 60. This adds a level of redundancy to the locking mechanism 1, allowing it to still operate if a switch malfunctions.

A resilient member 64, such as a coil spring, is preferably included in the locking mechanism 1 to bias the locking arm 30 toward the locked position. As can be seen in FIG. 4, one end of the resilient member 64 is attached to the upper member 40 of the locking arm 30, while the opposing end is attached to the frame 22. It will be appreciated that the resilient member 64 can be attached at a different location on the locking arm 30, such as the first end 32, middle portion 38, upper member 40 etc. The resilient member 64 encourages the locking arm 30 to move downward into the locked position as the cam 56 rotates in response to actuation of the closing switch 48. The resilient member 64 also provides a force that serves to retain the locking member 30 in the locked position, which must be overcome to move the locking arm 30 into the unlocked position.

Figure 7A:
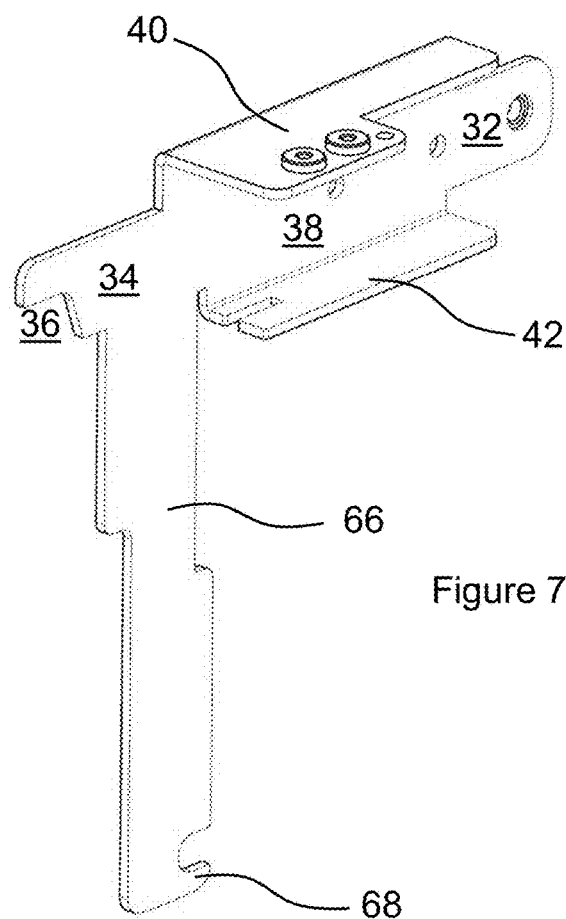
FIG. 7A is a perspective view of an embodiment of a locking arm of the locking mechanism shown in isolation.
Figure 7B:
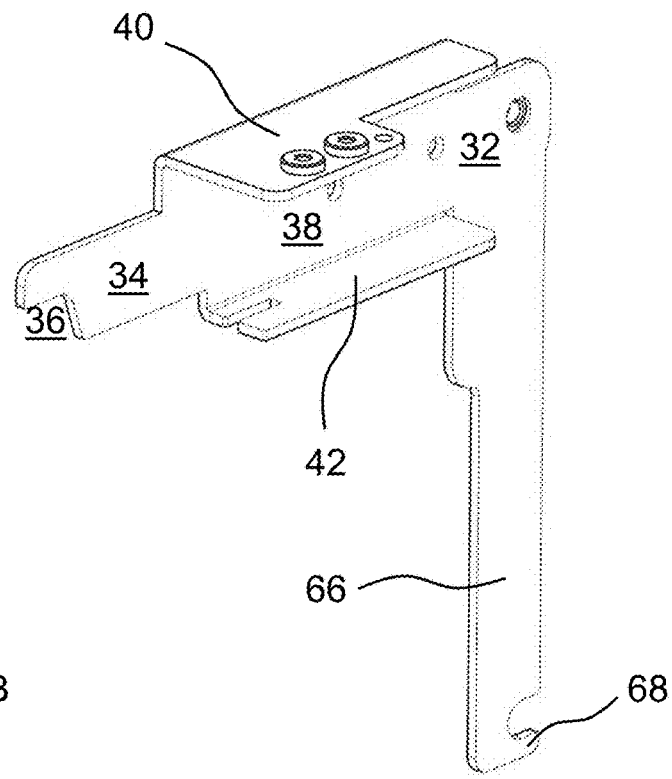
FIG. 7B is a perspective view of another embodiment of a locking arm of the locking mechanism shown in isolation.

The locking arm 30 can optionally include a manual release lever 66. The manual release lever 66 allows a user to manually displace the locking arm 30 from a locked position to an unlocked position. Two different embodiments of the manual release arm are shown in FIGS. 7A and 7B, in which the manual release lever 66 extends downward from a first end 32 of the locking arm 30, or from the second end 34 of the locking arm 30, respectively. Preferably, the manual release lever 66 has some form of gripping element 68 on or near its terminal end, such as a hook as illustrated. The manual release lever 66 allows a user to unlock the locking mechanism 1 in the case of power failure, malfunction or jamming of the locking mechanism, etc. by pulling the manual release lever 66 toward the front of the sterilizer 2. The manual release lever 66 causes the locking arm 30 to rotate about its hinge point 33, thereby raising the first end 32 of the locking arm 30 and allowing the pin 12 to be retracted back into the door 10.

When in use, as can be seen in FIGS. 8A-8D when the door 10 is in the open and unlocked position, i.e. the pins 12 are not deployed, and the orientation of the cam 56 displaces the locking arm 30 upward into an unlocked position. In this unlocked position, the first end 32 of the locking arm 30 hovers above the location of where the pin 12 will ultimately reside once it is deployed from the door 10.

Figure 10D:
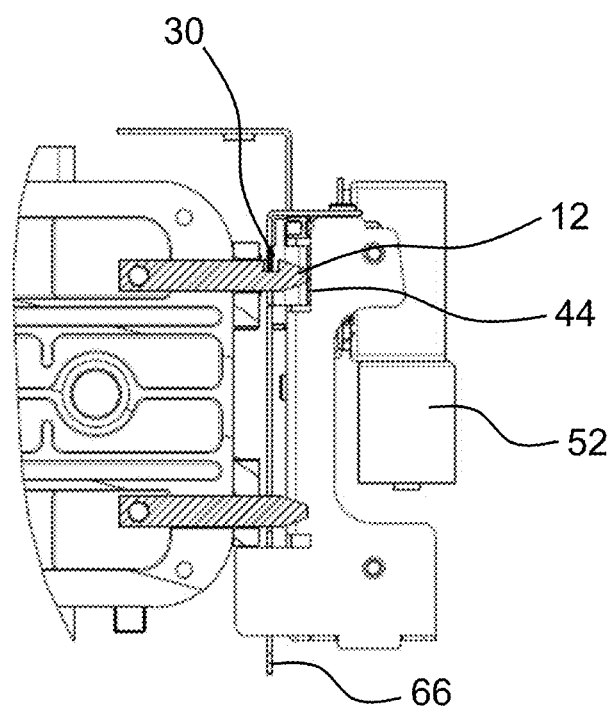
FIG. 10D is a view of the locking mechanism along lines B-B of FIG. 10C.

As can be seen in FIGS. 9A-9D, once the door 10 is closed, the knob 14 is turned to deploy the pins 12 through the guide apertures 20 of the guides 18. The pin 12 that is to engage the locking mechanism 1 passes through the cutaway portion 36 of the locking arm 30, and interacts with the sensor arm 44. The sensor arm 44 flexes, which actuates the closing switch 48 through either direct contact or through interacting with a closing switch lever 50 (See FIG. 9B) to inform the operating system that the door 10 is closed. Either in direct response to actuation of the closing switch 48, or in response to the user pressing a "lock" button on a control panel of the sterilizer 2, the operating system initiates the motor 52, which thereby rotates the camshaft 54 and cam 56. This rotational movement of the cam 56 along with the force applied by the resilient member 64 results in lowering of the locking arm 30 into a locked position, in which the second end 34 of the locking arm settles into the notch 28 of the pin 12 (See FIGS. 10C and 10D).

In the locked position, the locking arm 30 inhibits the ability of the pin to be retracted into the door until a user of the sterilizer 2 unlocks the locking mechanism 1. Typically, the user will press an "unlock" button on the control panel of the sterilizer 2, which sill signal the operating system to start the motor 52. The motor 52 will rotate the camshaft 54, with the cam 56 forcing the locking arm 30 up into the unlocked position against the resistance of the resilient member 64. When in the unlocked position, the locking arm 30 will no longer engage with the locking switch 60. This will trigger a signal being sent to the operating system so that it is aware that the locking mechanism is in the unlocked position. Thereafter, the operating system sends a signal to stop the motor 52, thereby stopping rotation of the camshaft 54 and cam 56. The position of the cam 56 holds the locking arm 30 in the unlocked position. With the locking mechanism 1 being unlocked, the pins 12 can be retracted, and the door 10 can be opened.

If there is a malfunction, power failure, etc., the user can pull the manual release lever 66, which when enough force is applied to overcome the resilient member 64, will temporarily raise the locking arm 30 up into an unlocked position so that the pins 12 can be retracted, and the door 10 can be opened.

What is claimed is:

1. A door locking mechanism for a sterilizer, the door locking mechanism abutting a door of the sterilizer, the door comprising an extendible portion that when extended engages with the door locking mechanism, the door locking mechanism comprising:
  a locking arm hingedly connected to a frame to permit the locking arm to move between a locked position and an unlocked position, the locking arm having a cutaway portion, the cutaway portion permitting the extendible portion of the door to extend therethrough;
  a sensor arm arranged adjacent to the locking arm, the sensor arm being flexible to permit the sensor arm to be at least partially displaced away from the locking arm in response to applied pressure to the sensor arm from the extendible portion of the door as it passes through the cutaway portion;
  a motor in communication with an operating system of the sterilizer;
  a camshaft actuated by the motor; a cam attached to the camshaft, the cam being in contact with the locking arm to move the locking arm between the locked position and the unlocked position;
  a closing switch positioned within the locking mechanism to detect displacement of the sensor arm, the closing switch being in communication with the operating system of the sterilizer such that when the closing switch detects displacement of the sensor arm it signals to the operating system that the door is in a latched position and actuates the cam via the camshaft and the motor to permit the locking arm to move into the locked position and engage with the extendible portion; a resilient member connected at a first end to the locking arm, and at a second end to the frame, the resilient member biasing the locking arm into the locked position; and
  a locking switch positioned within the locking mechanism to detect movement of the locking arm into the locked position, the locking switch being in communication with the operating system such that when the locking switch detects the movement of the locking arm into the locked position it signals to the operating system that the door is in the locked position and ceases operation of the motor.

2. The door locking mechanism of claim 1, wherein the locking arm has a first end, a second end, and a middle portion, the first end hingedly connected to the frame, the second end having the cutaway portion and being shaped and dimensioned to engage with and retain the extendible portion in an extended position, and the middle portion having an upper member and a lower member, each protruding outward from the locking arm.

3. The door locking mechanism of claim 2, wherein the sensor arm has a first end and a second end, the second end configured to be at least partially displaced away from the second end of the locking arm in response to applied pressure to the second end of the sensor arm from the extendible portion of the door as it passes through the cutaway portion.

4. The door locking mechanism of claim 3, wherein at least the second end of the sensor arm substantially mirrors the shape of the second end of the locking arm except for the cutaway portion.

5. The door locking mechanism of claim 3, wherein the first end of the sensor arm is fastened to the locking arm.

6. The door locking mechanism of claim 3, wherein the first end of the sensor arm is hingedly attached to the same point of the frame as the locking arm.

7. The door locking mechanism of claim 2, wherein the cam is in contact with the upper member to move the locking arm.

8. The door locking mechanism of claim 2, wherein the locking switch detects the lower member moving into the locked position.

9. The door locking mechanism of claim 1, further comprising:
  a manual release lever extending downward from the locking arm, whereby movement of the manual release lever rotates the locking arm between the locked position and the unlocked position.

10. The door locking mechanism of claim 9, wherein the manual release lever extends downward from a first end or a second end of the locking arm.

11. The door locking mechanism of claim 1, wherein the closing switch comprises a sensing lever, one end of the sensing lever being biased away from the closing switch, and wherein depression of the sensing lever by the sensor actuates the closing switch.

12. The door locking mechanism of claim 1, wherein the locking switch comprises a locking switch sensing lever, one end of the locking switch sensing lever being biased away from the locking switch, and wherein depression of the locking switch sensing lever by the lower member actuates the locking switch.

13. The door locking mechanism of claim 1, comprising more than one of the closing switches and/or the locking switches.

14. The door locking mechanism of claim 1, wherein the cam is an eccentric cam, a pear shaped cam, a snail shaped cam, or an elliptical shaped cam.

15. A door locking mechanism for a sterilizer, the door locking mechanism abutting a door of the sterilizer, the door comprising an extendible portion that when extended engages with the door locking mechanism, the door locking mechanism comprising:
  a locking arm having a first end, a second end, and a middle portion, the first end hingedly connected to a frame to permit the locking arm to move between a locked position and an unlocked position, the second end having a cutaway portion, the cutaway portion permitting the extendible portion of the door to extend therethrough, the second end being shaped and dimensioned to engage with and retain the extendible portion in an extended position, and the middle portion having an upper member and a lower member, each protruding outward from the locking arm;
  a resilient member connected at a first end to the locking arm, and at the second end to the frame, the resilient member biasing the locking arm downward into a locked position;
  a manual release lever extending downward from the locking arm, whereby movement of the manual release lever rotates the locking arm between the locked position and the unlocked position;
  a sensor arm having a first end and a second end and arranged adjacent to the locking arm, the sensor arm being flexible to permit the second end of the sensor arm to be at least partially displaced away from the second end of the locking arm in response to applied pressure to the second end of the sensor arm from the extendible portion of the door as it passes through the cutaway portion;

a motor in communication with an operating system of the sterilizer;

a camshaft actuated by the motor; a cam attached to the camshaft, the cam being in contact with the upper member to move the locking arm between the locked position and the unlocked position;

at least one closing switch positioned within the locking mechanism to detect displacement of the sensor arm, the closing switch being in communication with the operating system of the sterilizer such that when the closing switch detects displacement of the sensor arm it signals to the operating system that the door is in a latched position and actuates the cam via the camshaft and the motor to permit the locking arm to move into the locked position and engage with the extendible portion; and at least one locking switch positioned within the locking mechanism to detect movement of the lower member into the locked position, the locking switch being in communication with the operating system such that when the locking switch detects the movement of the lower member into the locked position it signals to the operating system that the door is in the locked position and ceases operation of the motor.

* * * * *